United States Patent
Park et al.

(10) Patent No.: US 10,080,090 B2
(45) Date of Patent: Sep. 18, 2018

(54) MEDICAL FEEDBACK SYSTEM BASED ON SOUND ANALYSIS IN A MEDICAL ENVIRONMENT

(71) Applicant: KONINKLIJKE PHILIPS N.V., Eindhoven (NL)

(72) Inventors: Mun Hum Park, Eindhoven (NL); Armin Gerhard Kohlrausch, Eindhoven (NL); Albertus Cornelis Den Brinker, Eindhoven (NL); Thomas Falck, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 87 days.

(21) Appl. No.: 14/352,484

(22) PCT Filed: Oct. 15, 2012

(86) PCT No.: PCT/IB2012/055603
§ 371 (c)(1),
(2) Date: Apr. 17, 2014

(87) PCT Pub. No.: WO2013/057652
PCT Pub. Date: Apr. 25, 2013

(65) Prior Publication Data
US 2014/0254808 A1 Sep. 11, 2014

Related U.S. Application Data

(60) Provisional application No. 61/547,912, filed on Oct. 17, 2011.

(51) Int. Cl.
*H04R 29/00* (2006.01)
*G16H 40/20* (2018.01)
(Continued)

(52) U.S. Cl.
CPC .......... *H04R 29/00* (2013.01); *G16H 40/20* (2018.01); *A61N 1/00* (2013.01); *G10L 13/00* (2013.01); *G10L 15/00* (2013.01)

(58) Field of Classification Search
CPC ..... G10L 13/00; G10L 15/00; G10L 21/0208; H04R 29/00; A61N 1/00; G16H 40/20
(Continued)

(56) References Cited

U.S. PATENT DOCUMENTS

| | | | |
|---|---|---|---|
| 2005/0110632 A1* | 5/2005 | Berezowski et al. | 340/521 |
| 2006/0012478 A1* | 1/2006 | Carmichel | G08B 3/10 340/552 |

(Continued)

FOREIGN PATENT DOCUMENTS

| | | |
|---|---|---|
| JP | 2002062186 A | 2/2002 |
| JP | 2005512608 A | 5/2005 |

(Continued)

OTHER PUBLICATIONS

Bonn et al, Noise Pollution in intensive care units reduced by simple measure, 1998.*

(Continued)

*Primary Examiner* — Davetta W Goins
*Assistant Examiner* — Kuassi Ganmavo (57) ABSTRACT

The present invention relates to a medical feedback system (100) based on sound analysis in a medical environment. With a sound scene analyzer (SSA, 10) being capable of analyzing and classifying an audio signal so as to obtain a list of one or more sound sources in the medical environment surrounding the patient, and a sound-level analyzer (SLA, 20) being capable of providing an indicator for perceived levels of corresponding sound from the list of sound sources, advanced sound analysis is possible. Finally, a sound classifier (SC, 30) is arranged for classifying said list of one or (Continued)

more sound sources in a medical environment with respect to a degree of avoidability, and generating a corresponding feedback signal (FEED, 50) for appropriate action by medical personal, patients and/or visitors.

14 Claims, 3 Drawing Sheets

(51) Int. Cl.
    *A61N 1/00*     (2006.01)
    *G10L 13/00*     (2006.01)
    *G10L 15/00*     (2013.01)

(58) Field of Classification Search
    USPC ........... 381/58, 56, 94.1–94.9; 704/221, 226, 704/232; 600/586, 301
    See application file for complete search history.

(56) References Cited

U.S. PATENT DOCUMENTS

| | | | |
|---|---|---|---|
| 2007/0183604 A1* | 8/2007 | Araki et al. | 381/58 |
| 2009/0005657 A1 | 1/2009 | Bodlaender et al. | |
| 2009/0005667 A1* | 1/2009 | Cui | A61B 5/04087 600/395 |
| 2009/0092261 A1* | 4/2009 | Bard | 381/71.1 |
| 2009/0196431 A1* | 8/2009 | Gregg | 381/56 |

FOREIGN PATENT DOCUMENTS

| | | | |
|---|---|---|---|
| JP | 2009520551 A | 5/2009 | |
| WO | 02086792 A2 | 10/2002 | |
| WO | 2007072412 A2 | 6/2007 | |
| WO | WO 2009153681 A1 * | 12/2009 | A61B 7/003 |

OTHER PUBLICATIONS

Mackenzie et al, Noise Levels and Noise Sources in Acute Care Hospital Wards, Building Serv Res Technol 2007.*
Reddy et al, Categorization of Environmental Sounds, Biol Cybern 2009.*
Mackenzie, D.J. et al. "Noise levels and noise sources in acute care hospital wards", Building Services Engineering Research and Technology Journal 1, vol. 28, pp. 117-131.
Aitken, R.J. "Quantitative noise analysis in a modern hospital". Arch Environ Health. Nov.-Dec. 1982; 37(6):361-4.
Lawson, N. et al. "Sount intensity and Noise evaluation in a critical care unit". American Journal of Critical Care. Nov. 2010, vol. 19, No. 6 pp. e88-e98.
Bonn D: "Noise pollution in intensive-care units reduced by simple measures", The LANCET, vol. 352, No. 9128, Aug. 22, 1998, p. 628.
Xie, H. et al. "Clinical review: The impact of noise on patients' sleep and the effectiveness of noise reduction strategies in intensive care units". Critical Care, (2009), 13:208.
Christensen, M. "Noise levels in a general surgical ward: a descriptive study". Nursing in Critical Care, vol. 12, Issue 4, pp. 188-197, Jul. and Aug. 2007.
Kahn, D.M. et al., "Identification and modification of environmental noise in an ICU setting", Chest 1998; 114;535-540.
Bao et al, "Psychoacoustic Active Noise Control With ITU-R 468 Noise Weighting and Its Sound Qualitly Analysis", 32nd Annual International Conference of the IEEE EMBS, 2010, pp. 4323-4326.

* cited by examiner

MEDICAL FEEDBACK SYSTEM BASED ON SOUND ANALYSIS IN A MEDICAL ENVIRONMENT

This application is a national stage application under 35 U.S.C. § 371 of International Application No. PCT/IB2012/055603 filed on Oct. 15, 2012 and published in the English language on Apr. 25, 2013 as International Publication No. WO/2013/057652, which claims priority to U.S. Application No. 61/547,912 filed on Oct. 17, 2011, the entire disclosures of which are incorporated herein by reference.

FIELD OF THE INVENTION

The present invention relates to a medical feedback system based on sound analysis in a medical environment. The present invention also relates to a corresponding method for providing feedback based on sound analysis in a medical environment, and a corresponding computer program product for implementing the invention.

BACKGROUND OF THE INVENTION

Noise levels in hospital setting may be surprisingly high, especially in intensive care units (ICU). Recent research studies also indicate that patients are negatively impacted by the high noise levels. Major noise sources in ICU environments may be attributed to the behavior of staff, including speech and other activities.

MacKenzie et al. ("Noise levels and noise sources in acute care hospital wards," Building Serv. Eng. Res. Technol. 28,2 (2007) pp. 117-131) have for example observed and classified noise sources in three 24-hour sessions in ICUs, and have identified a considerable number of avoidable, high-level noise events: rubbish bins, chair scraping, door closing/squeaking, cupboard door, and even opening of ring binders. A total of 30% of all noise events were characterized as totally avoidable, and a similar percentage as partially avoidable (like alarms; dropping objects; phone ringing).

There exist noise-level feedback systems that measure the sound level in building spaces and provide real time feedbacks in a simple format like traffic lights. These systems had been developed mainly for school environments, which recently and rather incidentally began to be used in hospitals.

However, the overall sound level is typically the only parameter on which such systems are designed to operate, and consequently the feedbacks may often be too ambiguous, providing little information on what the actual noise sources are.

The inventors of the present invention have appreciated that an improved medical feedback system and method is of benefit, and has in consequence devised the present invention.

SUMMARY OF THE INVENTION

It would be advantageous to achieve an intelligent way of providing feedback based on sound analysis in a medical environment. In general, the invention preferably seeks to mitigate, alleviate or eliminate one or more of the above mentioned disadvantages singly or in any combination. In particular, it may be seen as an object of the present invention to provide a method that solves the above mentioned problems, or other problems, of the prior art.

Thus, the above described object and several other objects are intended to be obtained in a first aspect of the invention by providing a medical feedback system based on sound analysis in a medical environment, the system comprising:

a sound scene analyzer (SSA), the sound scene analyzer being arranged for receiving an audio signal indicative of sound near a patient in the medical environment and being capable of analyzing and classifying the audio signal so as to obtain a list of one or more sound sources in the medical environment surrounding the patient, a sound-level analyzer (SLA), the sound-level analyzer being arranged for receiving an audio signal indicative of sound near a patient and being further arranged for receiving said list of one or more sound sources from the sound scene analyzer, the sound-level analyzer being capable of providing an indicator for perceived levels of corresponding sound from said list of sound sources, and a sound classifier (SC), the sound classifier being arranged for receiving said list of sound sources from the sound scene analyzer together with said indicator for perceived levels of corresponding sound from said list of sound sources from the sound-level analyzer, the sound classifier further being arranged for classifying said list of one or more sound sources in a medical environment with respect to, at least, a degree of avoidability, and generating a corresponding feedback signal.

The invention is particularly, but not exclusively, advantageous for obtaining a feedback system in medical context, where identifying or classifying the source of sounds around the patient is applied to generate, and where appropriate communicate corresponding feedback signals that may be utilized by the medical personal, and other relevant persons.

Thus, the invention provides an intelligent feedback system that is able to perform real-time sound analysis and classification. As the results of such analysis and classification, the feedback system may provide a list of primary sound sources with the information on whether they are avoidable or unavoidable and how much they contribute to the overall sound level. In particular, unwanted or undesirable sources of sound i.e. noise may be identified, and possibly minimized, preferably eliminated. Additionally, or alternatively appropriate counter measures can be considered to mitigate the effect of the sound sources on the acoustic environment around patients.

Depending on the outcome of the sound analysis, the feedback system may instantly provide appropriate feedback with required actions. At a given moment, the most dominant noise source may turn out to be, for example, unnecessary alarm sounds. In this case, the feedback system may advise hospital staff to take actions to turn down or off the alarms. If it is the speech activities between hospital staff that contributes mostly to the overall sound level, the system may directly advise them to consider lowering their voice, and so forth.

It may be noted that although the feedback system has been itemized into three separate modalities in the present formulation of the present invention, i.e. sound scene analyzer, sound level analyzer, and sound classifier, it is readily understood by the skilled person that in a practical implementation, e.g. on an appropriate computing device, the three modalities are typically integrated into a single processor implementing invention.

Nevertheless, the functional characteristics may be in various ways falling within the general scope and teaching of the present invention.

In a particular embodiment, the sound scene analyzer may comprise an audio feature extractor and classifier algorithm for analysis. More specifically, the audio feature extractor and classifier algorithm may be capable of extracting audio features representing physical, physiological, and/or psychological characteristics of the audio signal. Such levels may be described as features having low, medium, and/or high levels characteristics, respectively. Below will follow a more detailed explanation of these different levels of features extracted by the algorithm. In short, the algorithm performs a segmentation of the audio signal which is then analyzed in several levels.

Preferably, the sound scene analyzer may be capable, at least partly, of classifying the audio signal according to a list of predefined sound sources representative of the medical environment. More specifically, the following non-exhaustive list may comprise one of more of the following sound events or sources of sound:

speech, including between patients, between medical personal, and between medical personal and patients,
alarms produced by monitoring and/or surveillance devices in the said medical environment,
medical equipment,
footsteps,
movements or displacements of interior building parts, such as doors, windows, ventilators, and furniture,
metallic objects,
computer related events, such as mouse and keyboard operations, and/or,
consumer entertainment devices, such as music/video playback devices and television devices.

Advantageously, the sound scene analyzer may be capable of classifying audio signals based on a learning process being performed, at least initially, in the said medical environment. This is particularly beneficially if the medical environment has a unique sound environment.

Typically, the sound-level analyzer may comprise a psychoacoustic model for providing an indicator for perceived loudness, e.g. conventionally A or B weighting, or alternatively Zwicker loudness, or other hearing models readily available to the skilled person in acoustics. Possibly, more advanced model based on noisiness, sharpness, roughness, etc. may be applied within the teaching of the present invention.

Beneficially, the sound classifier may be further arranged for determining, based on the degree of avoidability, whether or not a feedback signal is to be outputted from the system. Thus, if for example the sound is unavoidable due to e.g. an essential alarm, then no feedback signal needs to be generated and transmitted.

In a particular embodiment, the sound classifier may further arranged for classifying the list of sound sources with respect to the estimated annoyance of the sound sources, more specifically the annoyance may be estimated with respect to patient's condition and/or the medical environment.

Beneficially, the generated feedback signal further may comprise an appropriate behavioral modification signal, the behavioral modification signal corresponding to one, or more, of the classified sound sources. Thus, if for example the sound source is classified as a loud speech, then a corresponding feedback signal to the relevant persons could be 'Please stop talking loud', 'Please lower your voice in this area', and so forth.

Similarly to the sound scene analyzer, the sound classifier may be capable of classifying said list of one or more sound sources based on a learning process being performed, at least initially, in the said medical environment.

In a particular advantageous embodiment, the sound classifier may be arranged for receiving patient specific information from an associated patient monitoring system in the medical environment, the sound classifier using the said patient specific information for classification with respect to, at least, the degree of avoidability. The patient monitoring system is, per se, another entity but could also be an integral part of the feedback system, or verse visa. The patient monitoring system may comprise, or be communicatively arranged with, various sensors for obtaining relevant patient data, e.g. electrical sensors, mechanical sensors, biochemical sensors. In a particular embodiment, the patient monitoring system may receive input based on manual observations, e.g. from a nurse.

Preferably, the feedback system may be arranged for monitoring a first plurality of patients with a second plurality of microphones, i.e. the number of microphones need not be equal to the number of patient. The microphones are arranged for communication with the feedback system, either by wire or wirelessly as will be readily appreciated by the skilled person. In one embodiment, there may also be just one patient and one microphone, e.g. a single patient approach for bed side application, for example in a private home.

Preferably, the feedback system may be arranged for communication with one or more feedback devices, the feedback devices being utilizable by medical personal, visitors, and/or patients. The feedback devices are arranged for communication with the feedback system, either by wire or wirelessly as will be readily appreciated by the skilled person. For example as mobile phones, monitors etc.

In a second aspect, the present invention relates to a method for operating a medical feedback system based on sound analysis in a medical environment, the method comprising:

providing a sound scene analyzer (SSA), the sound scene analyzer being arranged for receiving an audio signal indicative of sound near a patient in the medical environment and being capable of analyzing and classifying the audio signal so as to obtain a list of one or more sound sources in the medical environment surrounding the patient, providing a sound-level analyzer (SLA), the sound-level analyzer being arranged for receiving an audio signal indicative of sound near a patient and being further arranged for receiving said list of one or more sound sources from the sound scene analyzer, the sound-level analyzer being capable of providing an indicator for perceived levels of corresponding sound from said list of sound sources, and providing a sound classifier (SC), the sound classifier being arranged for receiving said list of sound sources from the sound scene analyzer together with said indicator for perceived levels of corresponding sound from said list of sound sources from the sound-lever analyzer, the sound classifier further being arranged for classifying said list of one or more sound sources in a medical environment with respect to, at least, a degree of avoidability, and generating a corresponding feedback signal.

In third aspect, the invention relates to a computer program product being adapted to enable a computer system comprising at least one computer having data storage means in connection therewith to control a medical feedback system based on sound analysis in a medical environment according to the second aspect. This aspect of the invention is particularly, but not exclusively, advantageous in that the present invention may be accomplished by a computer program product enabling a computer system to carry out the operations of the system of the first aspect of the invention when down- or uploaded into the computer system. Such a computer program product may be provided on any kind of computer readable medium, or through a network.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
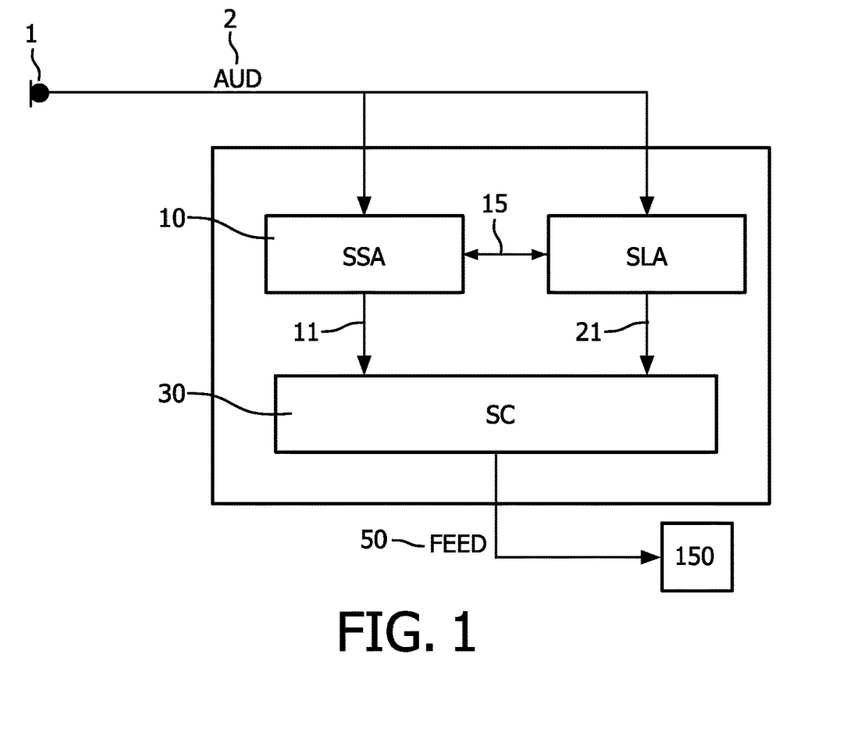
FIG. 1 shows a schematic drawing of a feedback system 100 according to the present invention.

FIG. 1 shows a schematic drawing of a feedback system 100 according to the present invention. The medical feedback system 100 is based on sound analysis in a medical environment where one or more microphones 1 produce an audio signal AUD 2 and transmit the signal to the system 100 as indicated schematically. The transmission may be done by wire or wirelessly as the skilled person would understand.

The system comprises a sound scene analyzer SSA 10, where the sound scene analyzer is arranged for receiving the audio signal AUD 2 indicative of sound near a patient (not shown) in the medical environment. Additionally, the analyzer SSA 10 is capable of analyzing and classifying the audio signal AUD 2 so as to obtain a list of one or more sound sources in the medical environment surrounding the patient. This will be further explained below.

The system 100 additionally comprises a sound-level analyzer SLA 20, which is also arranged for receiving the said audio signal AUD 2 as schematically indicated with the arrow connecting the microphone 1 with the SLA 20. Moreover, the sound-level analyzer 20 is further arranged for receiving the before mentioned list of one or more sound sources from the sound scene analyzer SSA 10 as indicated by arrow 15. It is however also envisioned that some information may be transmitted in opposite direction, i.e. from the sound-level analyzer SLA to the sound scene analyzer SSA to assist the SSA in performing its operation and function. From the information provided from SSA 10, the sound-level analyzer SLA 20 is capable of providing, by appropriate calculations and models, an indicator for perceived levels of corresponding sound from said list of sound sources. It should be noted that the SLA may provide a plurality of indicators, e.g. for various time windows, and/or different frequency bands.

Additionally, a sound classifier SC 30 is present in the system 100, the sound classifier SC 30 being arranged for receiving said list of sound sources from the sound scene analyzer SSA, as indicated by arrow 11, together with an indicator for perceived levels of corresponding sound from said list of sound sources from the sound-lever analyzer SLA 20, as indicated by arrow 21. The sound classifier CL is further arranged for classifying said list of one or more sound sources in a medical environment with respect to a degree of avoidability, and generating a corresponding feedback signal FEED 50. The degree of avoidability can, in straightforward embodiment, be a classification of a sound source or event as 'avoidable' or 'not avoidable'. However, degrees between these two opposite classifications are also contemplated within the teaching of the present invention.

The inventors have appreciated that the objective of improving the hospital environment by sound analysis in a feedback system 100 requires a targeted approach. To start with, the feedback indicators to the staff have to be meaningful (interpretable by these people) and also they have to relate to sound events which are within their span of control. Furthermore, the indicators should adequately capture the negative impact of the sound on the patient (meaningful).

These considerations already indicate that mere sound level monitoring is not sufficient. It also leads to a classification scheme which differs fundamentally from those found elsewhere, e.g. music analysis. Also, the span-of-control issue led to divide disturbing sound into avoidable and unavoidable. These considerations together with a screening of sound recordings made in the hospital led the present inventors to define a number of hospital specific classes and means or combination of means for identifying these.

There are classes of sound events that frequently happen in hospital environments, some of which, the inventors have found, may have significant impact on patient well-being not only due to their contribution to the overall noise level, but also due to their particular temporal and spectral characteristics (e.g. impulsiveness, etc.). By automatically identifying such classes of noise sources and notifying medical staff of their potential impact, therefore, subjective noise annoyance level can effectively be reduced, thus improving patients' sleep/rest quality, which may also positively influence on their recovery speed. In particular, the inventors have identified the following, non-exhaustive list of classes, which the feedback system will be trained to identify:

Speech (Patient-involved and Others)

From their own recordings and analysis of hospital noise, the inventors have identified that speech activities are the most dominant noise sources in terms of the average noise level. Therefore, it is important to discriminate speech from non-speech sounds. To detect the speech within the input signal, one may use several features including pitch range, mel-frequency cepstral coefficients (MFCC) and envelope variation. It is difficult to distinguish avoidable/non-avoidable speech since the context of the conversation should also be taken into account. Accordingly, inventors' approach, instead, is to identify patient-involved speech activities that are obviously unavoidable (from the patient's point of view), where other speech activities (e.g. between hospital staff) can be considered to be at least partly avoidable. In order to distinguish patient-involved conversation, various ways may be used, one of which can be a dedicated beam-forming technique using a multiple microphones, capturing audio signals only from a very limited area (the head of the patient bed). One of other examples can be the use of speaker identification technique. If the audio input is classified as speech, and if the input from the beam-former (or speaker identifier) indicates that it comes from the patient, then the system assumes that patient himself/herself is speaking Once patient speech is detected, all speech activities around the detected time (e.g., 5-10 minutes) will be considered to be patient-involved speech. Therefore, at the end of this process, speech will be further classified as patient-involved speech and other speech activities.

Alarms

Alarm is also one of the dominant noise sources in hospital. By producing alarm sounds, monitoring devices deliver warnings to medical staff. However, not all of the alarm sounds are unavoidable, since it was learned from field studies (and also from literature) that some less-urgent alarms (e.g. signaling the end of injection, etc.) are simply ignored without immediate actions taken by nursing staff. First, the classifier will identify all alarm sounds especially analyzing the tonality, harmonic structure and repetitiveness of input signal. Then, the system will observe how long the alarm sound continues without staff intervention. If the alarm lasts longer than a pre-determined threshold, then the feedback system will be activated to notify responsible medical staff. Also, the system can get the history of alarm sounds from patient monitoring systems, and learn how urgently (in medical sense) they have been reacted upon, based on which the threshold time for each type of alarm sound can be adjusted. It should however be very clear that the feedback system will give warnings only about the annoyance level of alarm sounds without any indication of the severity of medical situation (for example, the feedback system will never operate to force medical staff to mute essential alarms).

Medical Equipment Noise (E.G. Mechanical Ventilator)

For the patients in acute phases, e.g. those in intensive care unit, various medical devices are used to support their lives. However, these devices may constantly generate noise in the vicinity of patients' ears due to their positions in the room, which will negatively impact on their sleep/rest quality. Since the noise from such devices is continuous and repetitive, the feedback system will classify this class of noise based on rhythmicity and predictability.

Footsteps

For easy maintenance of hygiene, vinyl floor is common in hospital, which creates very distinctive footstep noises, which, it was observed, significantly contributes to the overall noise annoyance, although the average noise level is not so high. The feedback system will use the rhythmicity and spectral contents (e.g. MFCC), in order to learn and identify footsteps in a particular hospital environment.

Building Parts e.g. Door/Drawer/Cupboard Opening and Closing; Object Dropping; Thumps Similar to footsteps, this class of sound events does not contribute much to the average noise level, but have significant impact on patient sleep/rest quality due to the impulsiveness causing high instantaneous peak noise level. The feedback system will classify these events based on the measures of onset steepness and percussiveness.

Noise from Metallic Objects (e.g. Trolley, Bed Frame, etc.)

Similar to the two above classes, the physical level of metallic object noise may not be so high, but due to its unique timbre, the resultant annoyance may be significant. In order to identify this class of sound events, the feedback system will detect sharp spectral peaks that are not harmonics of each other.

Computer Related Events, e.g. Mouse Clicking

From inventors' own sound recordings, mouse clicking (dragging) noise was identified to be very disturbing (due to the proximity to patients' ears, as LCD monitor with mouse is commonly positioned to the bedside for nursing staff to access patient data), but hardly recognized as a potentially severe noise source. Very unique temporal spectral characteristics of mouse clicking noise will be used for the classification, which also partly adopts techniques developed to identify keyboard strike noise.

Music from TV/Radio

Sounds from TV or radio, when unwanted (e.g. coming from neighboring rooms) can be very disturbing. As speech in TV/radio contents may already be classified as 'Other speech activities', the feedback system will, instead, attempt to distinguish music from non-music contents, based on similar features that are used for the detection of speech (e.g. envelope variation of music is less than that of speech).

Most of the features described for the above classes are commonly used, for example, in speech analysis, music information retrieval, music recommendation system and other research areas (keyboard stroke). Their combination however, and adaptation and optimization of the combination particularly for tailored classes (based on the meaningful impact, staff-interpretable, span-of-control) for the hospital environments is an inventive step.

The following table summarizes the classes of sound events that may be used by the feedback system 100 and associated dominant class features:

| No. | Class of sound events | Features relevant for the classification | Remarks |
|---|---|---|---|
| 1 | Speech | Pitch range, mel-frequency cepstral coefficients (MFCC) and envelope variation | Patient-involved speech will be identified by, e.g., beam-forming techniques or speaker identification. |
| 2 | Alarm | Tonality, harmonic structure and repetitiveness | The system will learn potentially avoidable alarms based on the information from patient monitoring systems. |
| 3 | Medical equipment noise | Rhythmicity and predictability | |
| 4 | Footsteps | Rhythmicity and spectral contents (e.g. MFCC) | |
| 5 | Building parts opening and closing; object dropping; thumps | Onset steepness and percussiveness | |
| 6 | Noise from metallic objects | Non-harmonic sharp spectral peaks | |

| No. | Class of sound events | Features relevant for the classification | Remarks |
|---|---|---|---|
| 7 | Computer relevant events | Temporal spectral characteristics | |
| 8 | Music from TV/Radio | Features used for speech detection (e.g. envelope variation) | |

It should be noted that identified sound events from the list of sound sources are further classified into avoidable/unavoidable sound sources, possibly noise. If the classification by the sound scene analyzer is sufficiently accurate, some sound events may be easy to classify at this stage as avoidable or unavoidable. For example, object-dropping sound can be identified by the analyzer, and can directly be classified as avoidable. On the other hand, additional information may be required for this intelligent classification. To distinguish essential alarm sounds from unnecessary ones, for example, the sound classifier SC may have to be trained based on the information from a patient monitoring systems PMS and/or a hospital central monitoring database 250 (cf. FIG. 2): which alarm sounds the hospital staff had quickly responded to, given the condition of patient. A speaker identification system may also be employed to differentiate avoidable speech activities from the unavoidable (for example, a conversation in which the patient is involved is unavoidable). In addition, data from sleep/rest monitoring devices (e.g. based on actigraphy, electrodiagnosis (incl. EEG, ECG, EOG, EMG, etc.), camera-based movement detection, etc.) can be used to more accurately evaluate the influence of noise, which depends on the patient's state.

Figure 2:
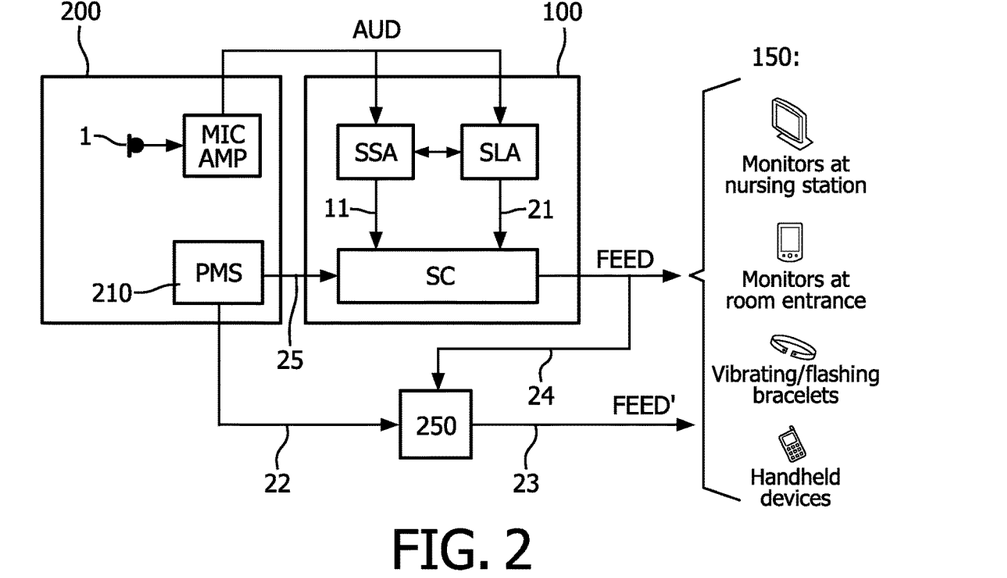
FIG. 2 shows a more detailed embodiment of the feedback system 100 according to the present invention.

FIG. 2 shows a more detailed embodiment of the feedback system 100 according to the present invention. In FIG. 2, the system 100 is shown together with a microphone 1 in a patient's room 200.

As explained above, for the acquisition of sound a microphone 1, or similar device, is placed in each patient's room 200, containing mainly a microphone 1 but also a microphone amplifier MIC AMP may be positioned locally.

With respect to the sound analysis, a computer with high computational power may host the feedback system 100, which 1) receives audio signal AUD from the patient's rooms 200 (only one room shown for clarity), 2) analyses the content and level of the possible noise, 3) determines whether the noise is avoidable or unavoidable, 4) determines whom the feedback should be delivered to and how, and 5) transmits the output to appropriate feedback devices 150.

Additionally, the feedback system may be integrated with a patient monitoring system PMS 210 shown schematically in the patient's room 200. The PMS may monitor physical condition and/or activity, and optionally also mental state, of the patient with appropriate medical monitoring devices available to the skilled person. The PMS may communicate with SC as indicated by arrow 25 i.e. the sound classifier is arranged for receiving patient specific information from the patient monitoring system PMS in the medical environment. The sound classifier CL may then use the said patient specific information for classification with respect to, at least, the degree of avoidability, the type of feedback signal to generate, and/or to who the signal should be transmitted.

The present invention may also be integrated with a central monitoring and surveillance unit 250 of the hospital or medical environment being monitored as indicated schematically with arrows 22 and 24. Possibly, the unit 250 may give feedback signal FEED' to feedback devices 150 as indicated by arrow 23. For the feedback signal FEED or FEED', there are shown various devices 150 that inform the designated personnel (mainly hospital staff, but also patients and their caretakers if necessary) of the contents and levels of the noise and the proposed actions. In FIG. 2, various feedback devices such as monitors at nursing stations and/or room entrances, bracelets giving tactile and/or visual response to the user, and handheld device (mobile phones etc.) are shown.

Though the feedback system 100 is shown as a separate entity, it is contemplated that the present invention may readily be integrated together with, or as a part of, the central monitoring and surveillance unit 250 of the hospital or medical environment being monitored.

Alternatively, the present invention may readily be integrated with, or as a part of, the patient monitoring system PMS 210. Alternatively, it is contemplated that the present invention may readily be integrated together with, or as a part of, a feedback device 150, e.g. as a part of a mobile device/phone, having sufficient computational resources and communicative abilities for implementing the teaching of the present invention.

Figure 3:
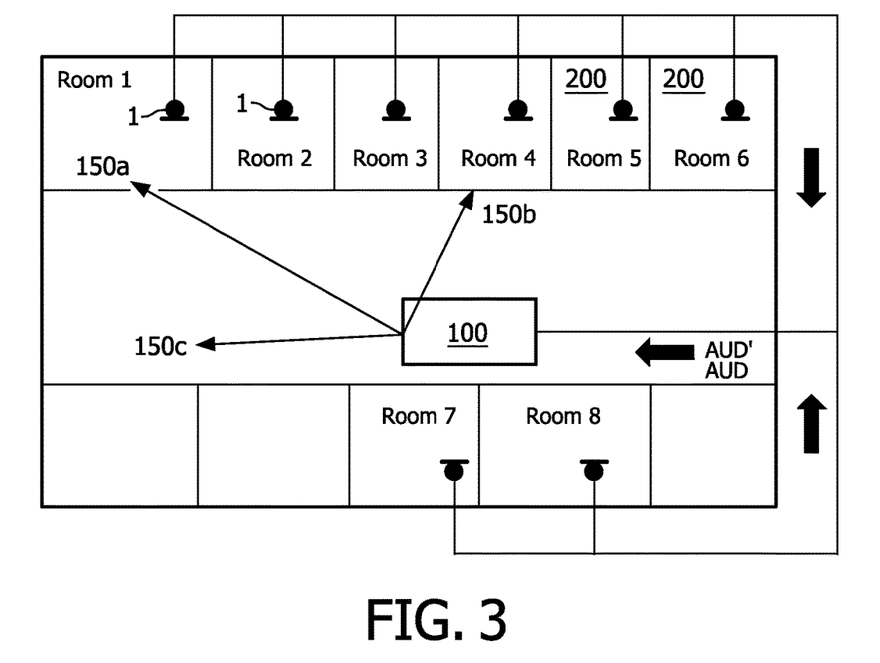
FIG. 3 shows an embodiment of the feedback system 100 according to the present invention implemented in a hospital environment with different patient rooms 200.

FIG. 3 shows an embodiment of the feedback system 100 according to the present invention implemented in a hospital environment with different patient rooms 200 (numbered Room 1 to Room 8) shown in the layout of a medical department, each room 200 having a microphone 1 as shown. Also three different feedback devices 150 are shown receiving feedback signal from the system 100 as indicated by the shown arrows, e.g.

feedback device 150a could be display device in Room 1, feedback device 150b could be a central display device for the medical department, and feedback device 150c could be handheld device carried by a medical staff member (not shown).

Figure 4:
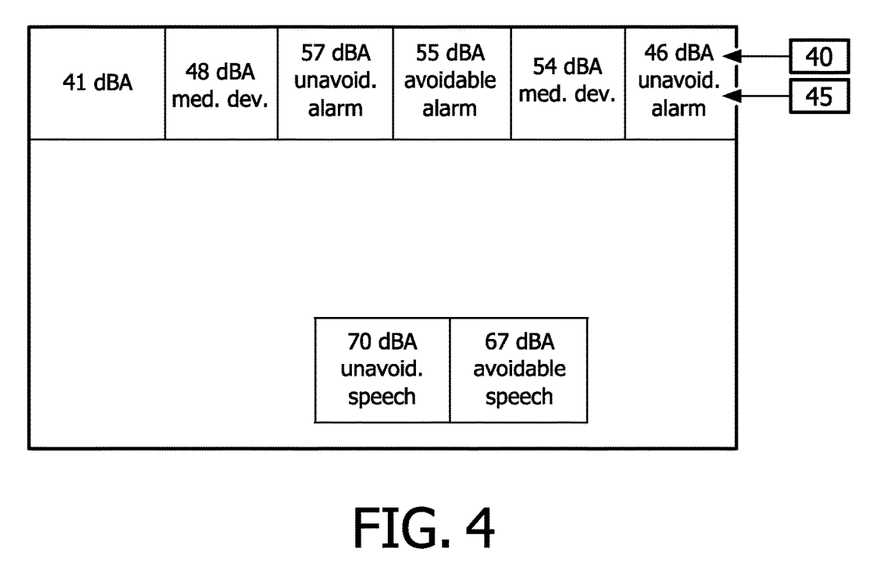
FIG. 4 shows a feedback example from the feedback system 100 provided an overview of sound levels and sound sources.

FIG. 4 shows a feedback example from the feedback system 100 providing an overview of sound level e.g. noise levels 40 and sound source e.g. noise sources 45 together with a classification of 'avoidable' or 'unavoidable' (abbreviated 'unavoid.'). The layout of FIG. 4 is the same as in FIG. 3. The feedback shown in FIG. 4 could for example be provided on a display 150b in FIG. 3.

Figure 5:
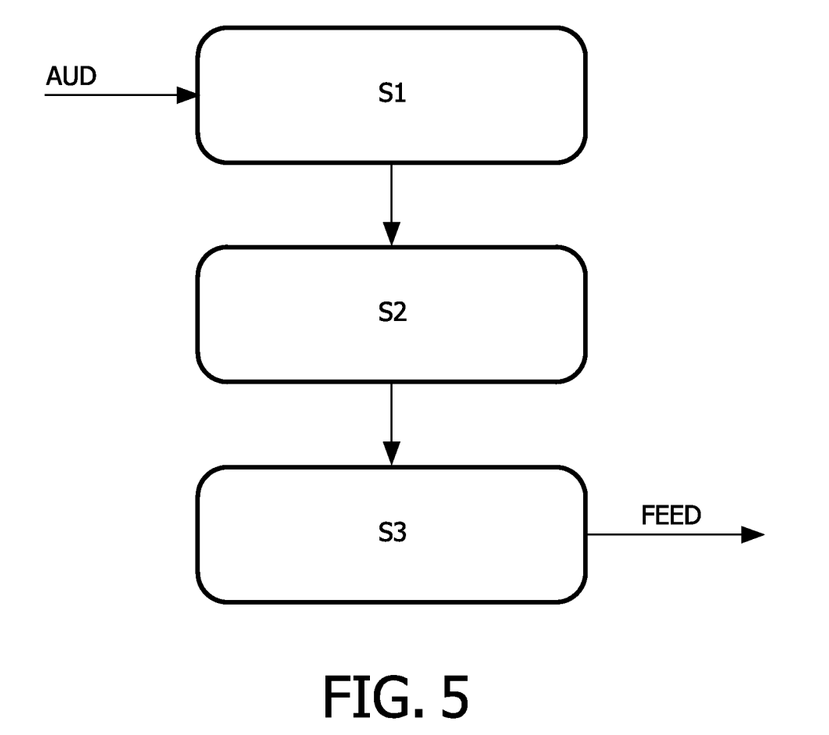
FIG. 5 is a schematic system-chart representing an outline of the operations of a method or a computer program product according to the present invention.

FIG. 5 is a schematic system-chart representing an outline of the operations of a method, or a corresponding computer program product according to the present invention.

The method or program comprising the steps of:

S1 providing a sound scene analyzer SSA 10, the sound scene analyzer being arranged for receiving an audio signal AUD indicative of sound near a patient in the medical environment and being capable of analyzing and classifying the audio signal so as to obtain a list of one or more sound sources in the medical environment surrounding the patient, S2 providing a sound-level analyzer SLA 20, the sound-level analyzer being arranged for receiving an audio signal AUD indicative of sound near a patient and being further arranged for receiving said list of one or more sound sources from the sound scene analyzer, the sound-level analyzer being capable of providing an indicator for perceived levels of corresponding sound from said list of sound sources, and S3 providing a sound classifier SC 30, the sound classifier being arranged for receiving said list of sound sources from the sound scene analyzer together with said indicator for perceived levels of corresponding sound from said list of sound sources from the sound-lever analyzer, the sound classifier further being arranged for classifying said list of one or more sound sources in a medical environment with respect to, at least, a degree of avoidability, and generating a corresponding feedback signal FEED 50.

In short, the present invention relates to a medical feedback system 100 based on sound analysis in a medical environment. With a sound scene analyzer SSA 10 being capable of analyzing and classifying an audio signal so as to obtain a list of one or more sound sources in the medical environment surrounding the patient, and a sound-level analyzer SLA 20 being capable of providing an indicator for perceived levels of corresponding sound from the list of sound sources, advanced sound analysis is possible. Finally, a sound classifier SC 30 is arranged for classifying said list of one or more sound sources in a medical environment with respect to a degree of avoidability, and generating a corresponding feedback signal FEED 50 for appropriate action by medical personal, patients and/or visitors.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

The invention claimed is:

1. A medical feedback system based on sound analysis in a medical environment, the system comprising:
a sound scene analyzer configured to:
receive an audio signal indicative of sound near a patient in the medical environment; and
analyzing and classifying the audio signal to obtain a list of one or more sound sources in the medical environment surrounding the patient,
a sound-level analyzer configured to:
receive the audio signal indicative of sound near a patient; and
receive said list of one or more sound sources from the sound scene analyzer; and
generate an indicator for perceived levels of corresponding sound from said list of sound sources, the indicator including at least one of a time window and a frequency band, and
a sound classifier configured to:
receive said list of sound sources from the sound scene analyzer together with said indicator for perceived levels of corresponding sound from said list of sound sources from the sound-lever analyzer;
classify said list of one or more sound sources in a medical environment with respect to a degree of avoidability associated with the generated indicators, the degree of avoidability including an avoidability scale ranging from avoidable to unavoidable,
generate a corresponding feedback signal based on the degree of avoidability of each of the classified one or more sound sources; and
output the corresponding feedback signal to at least one feedback device.

2. The medical feedback system according to claim 1, wherein the sound scene analyzer comprises an audio feature extractor and classifier algorithm.

3. The medical feedback system according to claim 2, wherein the audio feature extractor and classifier algorithm is programmed to extract audio features representing physical, physiological, and/or psychological characteristics of the audio signal.

4. The medical feedback system according to claim 3, wherein said list comprises one of more of the following sound events or sources of sound:
speech, including between patients, between medical personal, and between medical personal and patients,
alarms produced by monitoring and/or surveillance devices in the said medical environment,
medical equipment,
footsteps,
movements or displacements of interior building parts, such as doors, windows, ventilators, and furniture,
metallic objects,
computer related events, such as mouse and keyboard operations,
and/or,
consumer entertainment devices, such as music/video playback devices and television devices.

5. The medical feedback system according to claim 1, wherein the sound scene analyzer is configured to classify the audio signal according to a list of predefined sound sources representative of the medical environment.

6. The medical feedback system according to claim 1, wherein the sound scene analyzer is configured to classify audio signals based on a learning process being performed in the said medical environment.

7. The medical feedback system according to claim 1, wherein the sound-level analyzer comprises a psychoacoustic model configured to provide said indicator for perceived loudness.

8. The medical feedback system according to claim 1, wherein the sound classifier is configured to determine, based on the degree of avoidability associated with the generated indicators, whether or not a feedback signal is to be outputted from the system.

9. The medical feedback system according to claim 1, wherein the sound classifier is further configured to classify the list of sound sources with respect to the estimated annoyance of the sound sources.

10. The medical feedback system according to claim 1, wherein the feedback signal further comprises an appropriate behavioral modification signal, the behavioral modification signal corresponding to at least one of the classified sound sources; and control a noise source to reduce a level of noise based on the outputted feedback signal.

11. The medical feedback system according to claim 1, wherein the sound classifier is configured to classify said list of one or more sound sources based on a learning process being performed in the said medical environment.

12. The medical feedback system according to claim 1, wherein the sound classifier is configured to receive patient specific information from an associated patient monitoring system in the medical environment by using the said patient specific information for classification with respect to, at least, the degree of avoidability.

13. The medical feedback system according to claim 1, further including:

a plurality of microphones configured to monitor a corresponding plurality of patients by transmitting monitored noises to at least one of the sound scene analyzer and the sound level analyzer.

14. The medical feedback system according to claim 1, wherein the feedback system is configured to communicate with one or more feedback devices, the feedback devices being utilizable by medical personal, visitors, and/or patients.

* * * * *